United States Patent [19]

Duncan

[11] Patent Number: 4,713,843
[45] Date of Patent: Dec. 22, 1987

[54] SELF-SUPPORTING EAR PROTECTOR

[76] Inventor: Karen Duncan, 15 Palmer St., Cos Cob, Conn. 06870

[21] Appl. No.: 9,726

[22] Filed: Feb. 2, 1987

Related U.S. Application Data

[63] Continuation-in-part of Ser. No. 885,475, Jul. 14, 1986, abandoned.

[51] Int. Cl.$^4$ .............................................. A42B 1/06
[52] U.S. Cl. ........................................ 2/209; 128/151
[58] Field of Search ...................... 2/209, 174, 275; 128/151

[56] References Cited

U.S. PATENT DOCUMENTS

| | | | |
|---|---|---|---|
| 2,325,150 | 7/1943 | Sahlmann | 2/209 |
| 2,378,398 | 6/1945 | Feidler | 2/209 |
| 2,444,251 | 6/1948 | Goldman | 2/209 |
| 2,582,907 | 1/1952 | Kaufmann | 2/209 |
| 3,112,493 | 12/1963 | Greenberg | 2/209 |
| 3,751,813 | 3/1971 | Allen | 2/209 |

Primary Examiner—Louis K. Rimrodt
Assistant Examiner—J. L. Olds
Attorney, Agent, or Firm—Peter L. Berger

[57] ABSTRACT

A self-supporting ear protector includes a flexible core member formed from a flat, elongated rectangular sheet of a resilient, flexible plastic material substantially impervious to cold weather conditions, the sheet having opposite edges and the opposite edges abutting each other in a non-overlapping relation and heat sealed to each other to form the sheet into a continuous loop of substantially constant thickness having a general configuration of the ear to be protected, the continuous loop defining a first central opening therein; an outer protective exposed layer of material secured to one side of the sheet of plastic material in covering relation to the first central opening, the outer layer having an outer surface which can be imprinted; and an inner layer secured to the opposite side of the sheet of plastic material and having a second central opening in substantial alignment with the first central opening.

9 Claims, 5 Drawing Figures

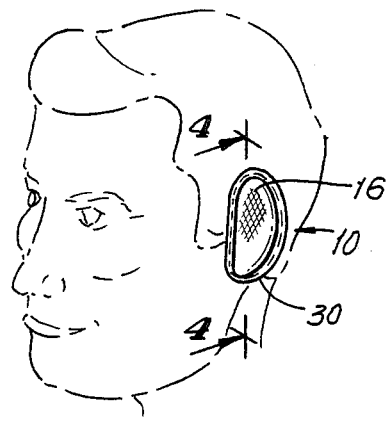
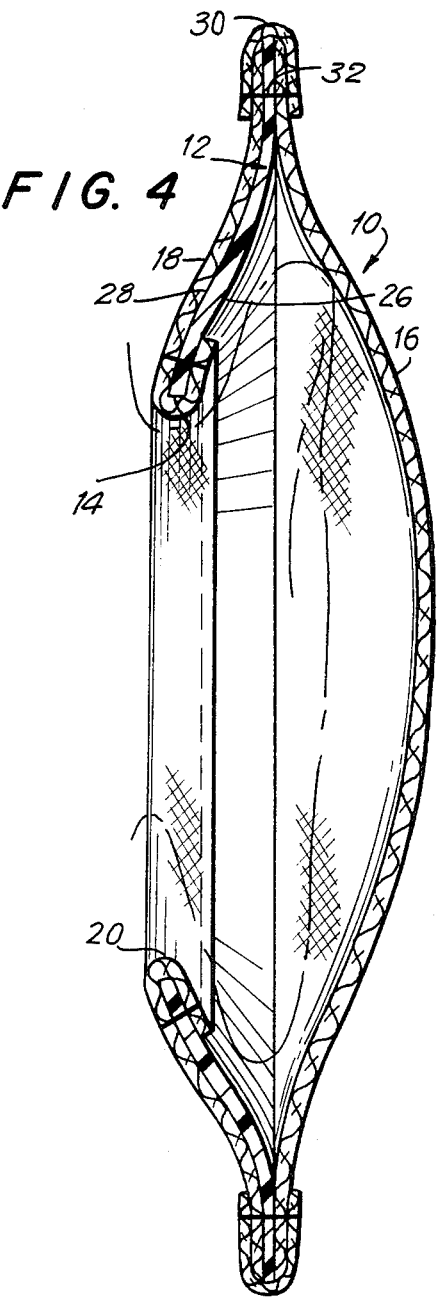
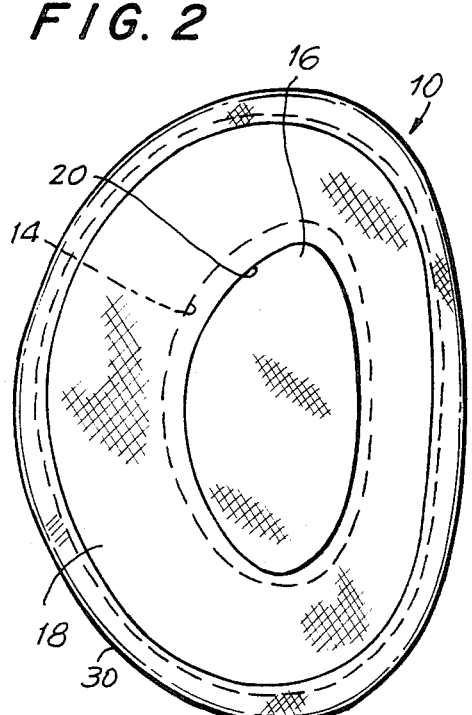
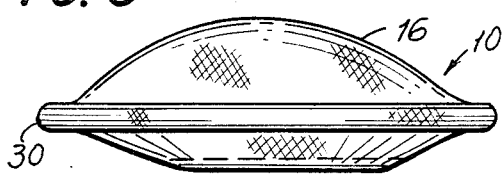

SELF-SUPPORTING EAR PROTECTOR

REFERENCE TO RELATED APPLICATION

This application is a continuation-in-part of U.S. patent application Ser. No. 885,475, filed July 14, 1986, now abandoned, to Karen Duncan and entitled Self-Supporting Ear Protector.

BACKGROUND OF THE INVENTION

This invention relates generally to ear protecting devices and, more particularly, is directed to a self-supporting device to be worn on the ear to keep the ear warm.

Ear protecting devices are well known in the prior art, for example, as disclosed in U.S. Pat. Nos. 2,325,150; 2,378,398; 2,582,907; and 3,112,493. Other devices of less relevance are disclosed in U.S. Pat. Nos. 3,922,725; 4,459,707; and 4,551,861.

Of the former patents U.S. Pat. No. 3,112,493 discloses an ear muff or protector having an inner core of an elongated planar configuration bent in a loop with opposite edges spaced slightly from each other. The opposite edges are secured to each other by a flexible, inelastic tape, thereby maintaining the inner core in a loop configuration with the opposite ends thereof spaced from each other. When in the loop configuration, the inner core defines a central, oval-shaped aperture through which the ear can fit. The ear protector is also formed with an outer protective exposed layer secured to the inner core in covering relation to the central aperture and an inner layer secured to the opposite side of the inner core and having an aperture in substantial alignment with the oval-shaped aperture in the inner core.

However, with this patent, since the opposite edges of the inner core are secured together in spaced apart relation by the inelastic tape, a slight bulge in the ear protector occurs thereat. In other words, the ear protector does not have a uniform thickness throughout the entire circumference thereof. As a result, there may be discomfort to the user of the ear protector.

The above other discussed patents fail to provide a solution to this problem. For example, in U.S. Pat. No. 2,378,398, the shell is stamped out of a flat plate, and the ends of the narrow strip are spaced from each other. The ends of the flat plate are held together by a piece of elastic material, such as a rubber band. However, in addition to the fact that securement by a rubber band is not very good, this patent also provides the same bulkiness by the addition of the rubber band, thereby providing discomfort to the user.

In U.S. Pat. No. 2,325,150, opposite ends of the inner core or blank are connected to each other in overlapping relation, thereby also increasing the thickness of the ear protector at this point, resulting in discomfort to the user.

U.S. Pat. No. 2,582,907 discloses an ear protector in which the inner core is made of a flat plate of rigid material such as cardboard or the like. However, it is clear from this patent that the flat plate is cut out in the shape of an ear and is not formed from a flat, substantially rectangular blank having its opposite ends secured together. Thus, although this patent provides a substantially constant thickness of the ear protector, it is difficult to manufacture and use, particularly since the ear protector must have a slightly convex configuration.

OBJECTS AND SUMMARY OF THE INVENTION

Accordingly, it is an object of the present invention to provide a self-supporting ear protector having a substantially constant and uniform thickness and feel throughout so as to be comfortable during use.

More importantly, it is another object of the present invention to provide a self-supporting ear protector having a flexible core layer made from a flat, elongated sheet of plastic material with opposite edges thereof in abutting relation and sealed to each other to form the sheet in a continuous loop.

It is another object of the present invention to provide a self-supporting ear protector in which opposite edges of the sheet of plastic material are joined to each other by heat sealing, welding or the like.

It is still another object of the present invention to provide a self-supporting ear protector which retains its protective characteristics under situations of extreme cold.

It is yet another object of the present invention to provide a self-supporting ear protector which will remain on the ear even though the wearer is active.

It is a further object of the present invention to provide a self-supporting ear protector which will retain its characteristics through repeated wearings and under conditions of extreme temperature and activity.

It is a still further object of the present invention to provide a self-supporting ear protector having a visible outer surface susceptible of being imprinted.

In accordance with an aspect of the present invention, an ear protector comprises a flexible core member including a flat, elongated sheet of a resilient, flexible plastic material substantially impervious to cold weather conditions and having opposite edges, the opposite edges abutting each other in a non-overlapping relation and sealed to each other to form the sheet into a continuous loop of substantially constant thickness having a general configuration of an ear to be protected, the continuous loop defining a first central opening therein; an outer protective exposed layer of material secured to one side of the sheet of plastic material in covering relation to the first central opening; and an inner layer secured to an opposite side of the sheet of plastic material and having a second central opening in substantial alignment with the first central opening.

The above and other objects, features and advantages of the present invention will become readily apparent from the following detailed description thereof which is to be read in connection with the accompanying drawings.

BRIEF DESCRIPTION OF THE DRAWINGS

FIG. 1 is a perspective view of the ear protector according to the present invention, being worn;

FIG. 2 is an inside elevational view of the ear protector of FIG. 1;

FIG. 3 is a top plan view of the ear protector of FIG. 1;

FIG. 4 is a cross-sectional view of the ear protector of FIG. 1, taken along line 4—4 thereof.

DETAILED DESCRIPTION OF A PREFERRED EMBODIMENT

Figure 5:
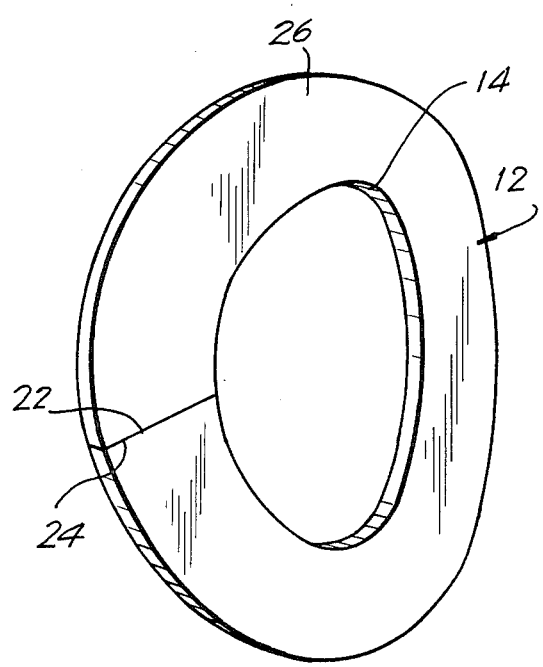
FIG. 5 is a perspective view of the flexible core member of the ear protector of FIG. 1.

Referring to the drawings in detail, a self-supporting ear protector 10 according to the present invention is generally formed with a flexible core member 12 formed in the general configuration of an ear to be protected and having a central oval-shaped opening 14 therein, an outer protective layer 16 secured to an outer surface of core member 12, and an inner layer 18 secured to the opposite surface of core member 12 and having a central oval-shaped opening 20 in substantial alignment with central opening 14.

Specifically, core member 12 is formed from a flat, elongated rectangular sheet of resilient, flexible plastic material which is substantially impervious to cold weather conditions. As an example, core member 12 can be formed from polyethylene, and preferably has a thickness of approximately 0.15 inches which is uniform throughout the sheet. The sheet of plastic material is configured in a continuous loop such that opposite edges 22 and 24 thereof are in a non-overlapping, abutting relation, as shown in FIG. 5. In such a configuration, opposite edges 22 and 24 are secured to each other by heat sealing, welding or the like so as to maintain the sheet in a continuous loop having the general configuration of an ear to be protected. With this manner of forming core member 12, core member 12 is formed with the aforesaid central opening 14. It will be appreciated that, because of the manner of formation of core member 12, core member 12 is formed in a slightly bent configuration, having a convex inner surface 26 and a concave outer surface 28, as best shown in FIG. 4 so as to better conform to the configuration of the ear to be protected.

It is an important aspect of the present invention that edges 22 and 24 are connected to each other in an abutting, non-overlapping relation. As such, the thickness of core member 12 is uniform throughout, and no additional bulky materials, such as straps, elastic bands or the like are needed to secure the edges together. Accordingly, there is a more comfortable feel to the wearer.

Outer protective layer 16 is exposed to the ambient elements and is secured to outer surface 28 of core member 12 at the outer periphery thereof so as to cover core member 12 and opening 14 therein.

Inner layer 18 is secured to the opposite inner surface 26 of core member 12 at the outer periphery thereof such that central opening 20 thereof is in substantial alignment with central opening 14 of core member 12.

To secure outer protective layer 16 and inner layer 18 to core member 12, a reinforcing material 30 is preferably wrapped about inner layer 18, core member 12 and outer protective layer 16 at the outer periphery of core member 12, and stitching 32 is used to secure reinforcing material 30, inner layer 18, core member 12 and outer protective layer 16 together, as shown in FIG. 4.

In operation, due to the flexibility of the ear cartilege, the ear can be inserted through openings 20 and 14, as shown in FIG. 4. Once the ear is inserted, ear protector 10 is bent to conform to the ear surface. Specifically, due to the flexibility of core member 12, core member 12 is flexed toward the ear, allowing the ear protector to hug the ear and be held thereon.

As will be appreciated, because ear protector 10 hugs the ear, any bulges or the like in ear protector 10 would cause discomfort to the wearer. In the aforementioned prior art patents, where the central core member was formed from an elongated sheet of material, the opposite edges thereof were secured in an overlapping relation or were secured with an additional material placed on the core member, such as a rubber band or the like. Such construction, however, as aforesaid, creates a bulkiness or variation in thickness in the core member, and thereby in the ear protector, which causes discomfort to the wearer. The present invention, by providing the edges of the sheet of plastic material in a non-overlapping, abutting relation and by sealing the same in such a position, creates a core member 12 with a constant thickness throughout, thereby rendering use of ear protector 10 comfortable to the wearer. Thus, ear protector 10 can be worn in total comfort, giving the wearer warmth with the security that the ear protector will not dislodge or otherwise fail to protect the ear during periods of activity under cold weather conditions, such as skiing or sledding.

As another feature of the present invention, the outer surface of outer protective layer 16 is configured so that it can be imprinted with a message, insignia, trademark or the like, as desired. By providing such an imprinting surface, ear protector 10 may serve as a premium item.

Having described a specific preferred embodiment of the invention with reference to the accompanying drawings, it will be appreciated that the present invention is not limited to that precise embodiment, and that various changes and modifications can be effected therein by one of ordinary skill in the art without departing from the spirit or scope of the invention as defined in the appended claims.

What is claimed is:

1. An ear protector comprising:
    a flexible member including a flat, elongated sheet of a resilient, flexible plastic material substantially impervious to cold weather conditions and having opposite edges, said opposite edges abutting each other in a non-overlapping relation and sealed to each other to form said sheet into a continuous loop of substantially constant thickness having a general configuration of an ear to be protected, said continuous loop defining a first central opening therein;
    an outer protective exposed layer of material secured to one side of said sheet of plastic material in covering relation to said first central opening; and
    an inner layer secured to an opposite side of said sheet of plastic material and having a second central opening in substantial alignment with said first central opening.

2. An ear protector according to claim 1; wherein said opposite edges are heat sealed to each other.

3. An ear protector according to claim 1; wherein said opposite edges are welded to each other.

4. An ear protector according to claim 1; wherein said sheet of plastic material is made of polyethylene.

5. An ear protector according to claim 1; wherein said core member has a substantially constant thickness of 0.15 inches.

6. An ear protector according to claim 1; wherein said outer protective layer has an exposed surface which may be imprinted.

7. An ear protector according to claim 1; wherein said core member has an outer concave surface and an inner convex surface.

8. An ear protector according to claim 1; further including reinforcing means for securing said outer protective layer, said inner layer and said core member together at an outer periphery of said ear protector.

9. An ear protector according to claim 8; wherein said reinforcing means includes a reinforcing material wrapped about the outer periphery of said ear protector and a stitching material for securing together said reinforcing material, said outer protective layer, said inner layer and said core member thereat.

* * * * *